US006620121B1

(12) United States Patent
McCotter

(10) Patent No.: US 6,620,121 B1
(45) Date of Patent: Sep. 16, 2003

(54) PULSE WAVE GENERATOR FOR CARDIOPULMONARY BYPASS AND EXTRACORPOREAL OXYGENATION APPARATUS

(75) Inventor: Craig J. McCotter, Charleston, SC (US)

(73) Assignee: East Carolina University, Greenville, NC (US)

( * ) Notice: Subject to any disclaimer, the term of this patent is extended or adjusted under 35 U.S.C. 154(b) by 0 days.

(21) Appl. No.: 09/571,773

(22) Filed: May 16, 2000

Related U.S. Application Data

(60) Provisional application No. 60/136,156, filed on May 27, 1999.

(51) Int. Cl.[7] .......................... A61M 37/00; A61M 1/36; A61N 1/362
(52) U.S. Cl. ...................... 604/6.11; 604/6.1; 604/4.01; 422/44; 600/16
(58) Field of Search ..................... 422/44, 45; 604/4.01, 604/5.01, 6.1, 6.11, 6.14, 6.16, 28, 30, 914, 132, 151; 623/3.1, 3.16, 3.17, 3.26; 417/394–95, 447, 474, 476, 477.3, 480, 540, 543, 477.12; 600/16, 18

(56) References Cited

U.S. PATENT DOCUMENTS

| | | | |
|---|---|---|---|
| 3,656,873 A | 4/1972 | Schiff | 417/395 |
| 3,750,644 A | 8/1973 | Ragsdale | 128/1 D |
| 3,877,843 A | 4/1975 | Fischel | 417/394 |
| 4,086,653 A | 4/1978 | Gernes | 364/564 |
| 4,250,872 A | 2/1981 | Tamari | 128/1 D |
| 4,492,531 A | * 1/1985 | Kenji et al. | 20/321.65 |
| 4,610,656 A | * 9/1986 | Mortensen | 604/6.14 |
| 4,662,829 A | * 5/1987 | Nehring | 417/395 |
| 4,976,593 A | 12/1990 | Miyamoto | 417/476 |
| 5,129,789 A | * 7/1992 | Thornton et al. | 417/53 |
| 5,300,015 A | * 4/1994 | Runge | 600/16 |
| 5,772,691 A | 6/1998 | Routh et al. | 607/9 |
| 5,820,579 A | 10/1998 | Plotkin | 604/4 |
| 5,931,648 A | * 8/1999 | Del Canizo | 417/478 |

OTHER PUBLICATIONS

International Search Report PCT/US00/13494, dated Oct. 10, 2000.

* cited by examiner

Primary Examiner—Angela D. Sykes
Assistant Examiner—Patricia Bianco
(74) Attorney, Agent, or Firm—Myers Bigel Sibley & Sajovec

(57) ABSTRACT

The present invention is a cardiopulmonary bypass and extracorporeal oxygenation apparatus that provides a pulsatile blood flow output. The apparatus comprises: a primary pump, which primary pump is preferably a continuous pump; an oxygenator in fluid communication with the primary pump; a pulse wave generator in fluid communication with the oxygenator and positioned downstream from the primary pump. The pulse wave generator comprises: (i) a collapsible chamber having an inlet opening and an outlet opening formed therein; (ii) a first one-way valve connected to the inlet opening and positioned to permit the flow of blood from the primary pump through the collapsible chamber. A compression assembly is operatively associated with the collapsible chamber and configured to alternately compress said collapsible chamber and permit the expansion of the collapsible chamber.

15 Claims, 2 Drawing Sheets

PULSE WAVE GENERATOR FOR CARDIOPULMONARY BYPASS AND EXTRACORPOREAL OXYGENATION APPARATUS

RELATED APPLICATIONS

This application claims priority from commonly owned, provisional application Ser. No. 60/136,156 filed May 27, 1999, the disclosure of which is incorporated by reference herein in its entirety.

FIELD OF THE INVENTION

The present invention concerns a pulse wave generator for incorporation into cardiopulmonary bypass apparatus and extracorporeal membrane oxygenation apparatus, and apparatus that includes such a pulse wave generator.

BACKGROUND OF THE INVENTION

Many complications following cardiopulmonary bypass (CPB) may be related to aberrant autonomic control of vascular function, which in turn may result from the lack of pulsatile perfusion pressures in most CPB circuits, leading to a loss of baroreceptor-mediated control and decrease in blood flow and oxygen delivery. Accordingly, it would be extremely desirable to provide CPB apparatus that provides both precise control of blood flow in a manner that mimics natural blood flow from the heart. Unfortunately, current apparatus falls short of these goals.

For example, U.S. Pat. No. 4,250,872 to Tamari discloses a cardiopulmonary bypass and extracorporeal oxygenation system comprising an oxygenator, a roller pump, and a pulse wave generator. The pulse wave generator is formed of a collapsible chamber, and is pneumatically driven. Thus the waveform of the output fluid from the pulse wave generator would be generally sinusoidal in nature, and would not accurately emulate the sharper peak waveform of the fluid output of the human heart.

U.S. Pat. No. 3,656,873 to Schiff discloses a pulsatile by-pass blood pump comprising a first "atrium" chamber and a second "ventricle" chamber which are said to be similar in design and function to corresponding portions of a natural heart. The ventricle chamber has a pair of flap valves on the inlet and outlet thereof. The atrium chamber serves as a buffer between the pulsatile operation of the ventricle, as well as the pressure within the inlet line by adjusting the size thereof. The atrium chamber does not serve as a pump. It would be difficult to precisely control the overall volume of blood flow with this type of pump.

In view of the foregoing, there is an ongoing need for cardiopulmonary bypass apparatus that incorporates a simple and convenient pulse wave generator that serves to mimic natural blood flow in the subject.

SUMMARY OF THE INVENTION

The present invention is a cardiopulmonary bypass and extracorporeal oxygenation apparatus that provides a pulsatile blood flow output. The apparatus comprises:

(a) a primary pump, which primary pump is preferably a continuous pump;

(b) an oxygenator in fluid communication with the primary pump;

(c) a pulse wave generator in fluid communication with the oxygenator and positioned downstream from the primary pump; the pulse wave generator comprises:

(i) a collapsible chamber having an inlet opening and an outlet opening formed therein;

(ii) a first one-way valve connected to the inlet opening and positioned to permit the flow of blood from the primary pump through the collapsible chamber; and (d) a compression assembly operatively associated with the collapsible chamber and configured to alternately compress said collapsible chamber and permit the expansion of the collapsible chamber.

The use of a continuous pump feeding into a pulse chamber that is fitted with a one way valve provides unexpected advantages in the present invention. It would seem undesirable to pump blood with a continuous pump into one-way valve that would be closed during a portion of the pumping cycle (due to a relatively greater pressure in the pulse wave generator during the compression cycle thereof). This feature, however, creates a more rapid pressure transition (that is, a sharper pressure peak) in the pulsatile flow output of the pulse wave generator, rather than more sinusoidal pressure transitions created by prior art devices. Without wishing to be bound to any particular theory of the invention, the competing pressure fronts on the valves apparently cause them to open and close rapidly. The sharper pressure peaks created by the apparatus of the present invention are more like that of a natural heart, yet the present invention retains the advantage of control of volume of flow provided by a continuous pump.

The foregoing and other objects and aspects of the present invention are explained in detail in the following drawings and specification.

DETAILED DESCRIPTION OF PREFERRED EMBODIMENTS

In brief, the invention is a cardiopulmonary bypass and extracorporeal oxygenation system that incorporates a pulse wave generator. The system comprises a primary pump, an oxygenator, and a pulse wave generator. A blood outlet line or conduit from the patient is typically taken from the patient's right atrium or from the patient's vena cava. The primary pump is preferably a continuous pump such as a roller pump (as illustrated) or a centrifugal pump. The pulse wave generator, which is located downstream from the primary pump, is a collapsible chamber driven by an external lever arm that has a pair of one-way valves at the inlet and outlets thereof. The valves permit blood to flow from the primary pump through the pulse wave generator, but not backwards from the patient through the pulse wave generator. Blood is typically returned to the patient from the pulse wave generator via a line or conduit to the aorta.

Figure 1:
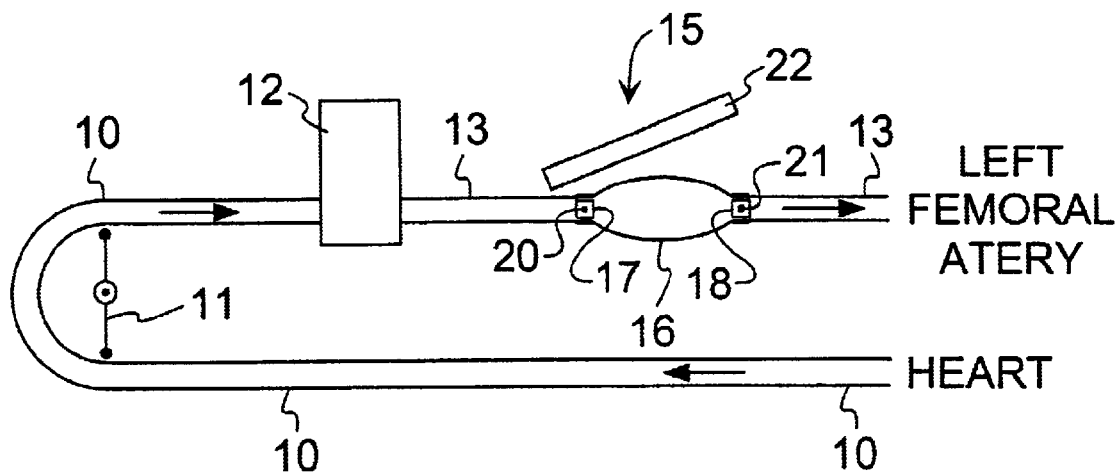
FIG. 1 is a schematic illustration of an apparatus of the present invention.

A specific example of an apparatus of the present invention is set forth in FIG. 1. The apparatus comprises an inlet line 10 which is connected to the heart of the subject in accordance with standard techniques, and a SARNS 5000 (available from SARNS, Ann Arbor, Mich., USA) roller pump 11 as the continuous pump. A membrane oxygenator 12 (specifically, an Affinity Hollow Fiber Oxygenator, Model no. 141006-01 from AVECOR Cardiovascular Inc., Plymouth, Minn. 55441 USA) is positioned on the inlet line downstream, or distal to, the pump. An outlet line 13 exits the oxygenator and returns blood (for demonstrative purposes) to the left femoral artery of the subject (more preferably for clinical purposes, return is to the aorta). A pulse wave generator 15 is positioned in the outlet line, with the pulse wave generator comprising a collapsible chamber or bulb 16, having an inlet opening 17 and an outlet opening 18, a one way valve 20 positioned in the inlet opening, and a one way valve 21 positioned in the outlet opening. The valves are oriented so that blood may flow from the pump to the patient, but not from the patient back towards the pump (the primary object of the valves is, however, to achieve a sharp pressure spike in the blood flow rather than a sinusoidal wave-form, rather than to prevent back-flow of blood from the patient to the pump in this direction). The one-way valves were obtained from Sierra Echlin Co. of Litchfield, Ill. USA. The bulb was connected to the inlet and outlet lines by straight disposable plastic connectors with LUER-LOK™ fittings, ½"×⅜", obtained from Baxter Healthcare Corp., Bentley Division, in Irvine, Calif., 92714 USA.

For demonstrative purposes, a manually operated lever arm 22 is used to as the compression assembly to compress the bulb 16. The lever arm is constructed of two 1 and ½ inch square wood members 3½ feet in length joined with a hinge. The bulb was held in place by wire guide wires to one of the wood members and placed six inches from the hinge. Of course, any type of compression assembly can be used to as a compression means for compressing the collapsible chamber in carrying out the present invention in addition to that described above, including but not limited to electrical, pneumatic or hydraulic motive devices, which can act directly or indirectly upon the collapsible chamber such as through a lever arm, cam or cam assembly, hydraulically or pneumatically driven piston, an expandable chamber such as a hydraulically or pneumatically driven bladder, etc. The compression assembly can be driven by hardware and/or software and (where necessary) appropriate interface devices, all in accordance with techniques that will be readily apparent to those skilled in the art.

Any continuous pump can be used as the primary pump, including but not limited to roller pumps and centrifugal pumps. An advantage of the present invention is that it can be implemented in a variety of different CPB systems.

Any type of one-way valve may be employed in carrying out the present invention, including but not limited to ball valves and flap valves. While it is currently preferred to configure the apparatus with a pair of one way valves, one each at the inlet and outlet of the collapsible chamber, in an alternate embodiment of the invention, a single one way valve is positioned in either the inlet or outlet opening of the collapsible chamber (preferably the inlet opening). The other valve may be replaced with a suitable adapter, such as an open Bentley ½ to ⅜ inch double male step down adapter.

The collapsible chamber is preferably constructed in the form of a bulb, made of a unitary piece of flexible, elastic, polymeric material. The material preferably has a "memory" such that when it is compressed and compression is released the chamber returns to its previous configuration. For demonstrative purposes, a Sierra primer bulb manufactured by the Echlin Co. of Litchfield, Ill., USA, is used as the collapsible chamber. The chamber should have a volume of approximately 50 or 60 cubic centimeters to about 90 or 100 cubic centimeters. Preferably, all parts in contact with the patient's blood are formed from non-corrosive and pyrogen free materials suitable for medical and/or veterinary use. For example, blood conduit tubing can be formed of a biocompatible polymer such as PELLETHANE™, manufactured by Dow, Inc., or polyvinyl chloride. The chamber has an interior wall that is formed of a noncoagulating or anticoagulant material, such as a heparin coating. Our bulb was made of a rubber material and the interior soaked in heparin solution to form an anticoagulant coating therein in accordance with standard techniques.

Figure 3:
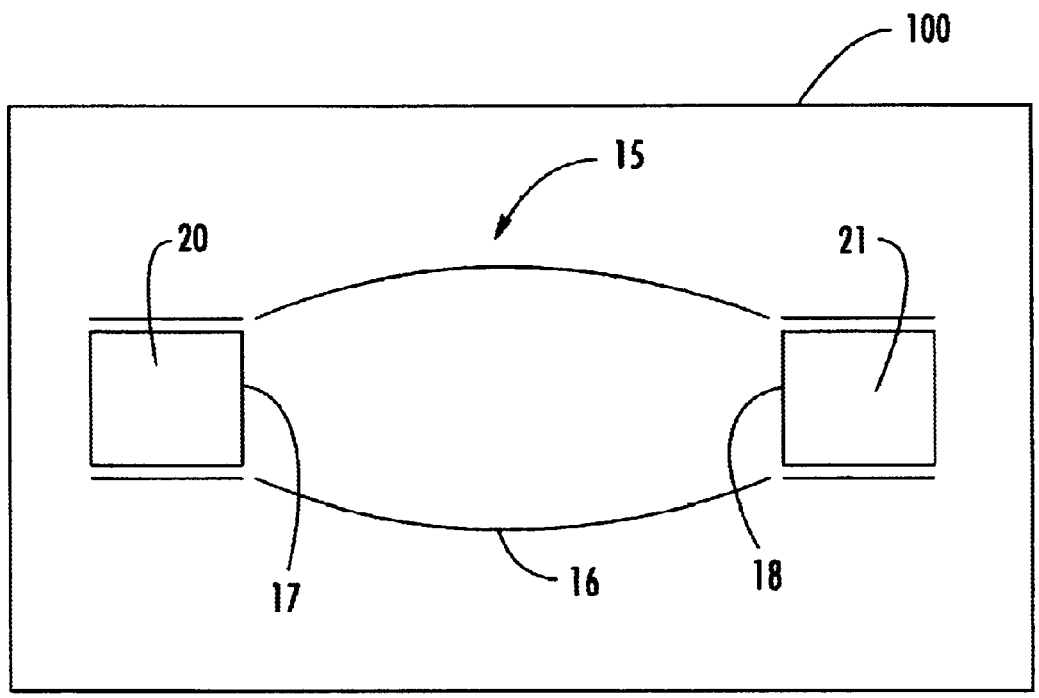
FIG. 3 is a schematic illustration of an apparatus of the present invention in an aseptic package.

Referring to FIG. 3, the pulse wave generator 15 can be conveniently provided as a separate, disposable unit 100. For such purposes, the pulse wave generator 15 is preferably provided as a sterile part or in sterile form, sealed in an aseptic package such as unit 100, which package may be opened at the site of the CPB apparatus and installed therein.

Numerous variations and additional features can be incorporated into the foregoing devices. Additional elements can be added to the CPB apparatus, such as filters, heaters, bubble traps, air detectors and other alarm circuits, etc. While the present invention is contemplated primarily for use on human patients or subjects, the invention may also be used on animal subjects such as dogs and cats for veterinary purposes.

The present invention is explained in greater detail in the following non-limiting Examples.

EXAMPLE 1

Effect of Pulsatile vs. Non-Pulsatile Cardiopulmonary Bypass (CPB) on Baroreceptor Resetting The purpose of this study was to determine the impact of pulsatile vs. non-pulsatile cardiopulmonary bypass (CPB) on baroreceptor resetting and the efficiency of the pulsatile CPB design described above.

Figure 2:
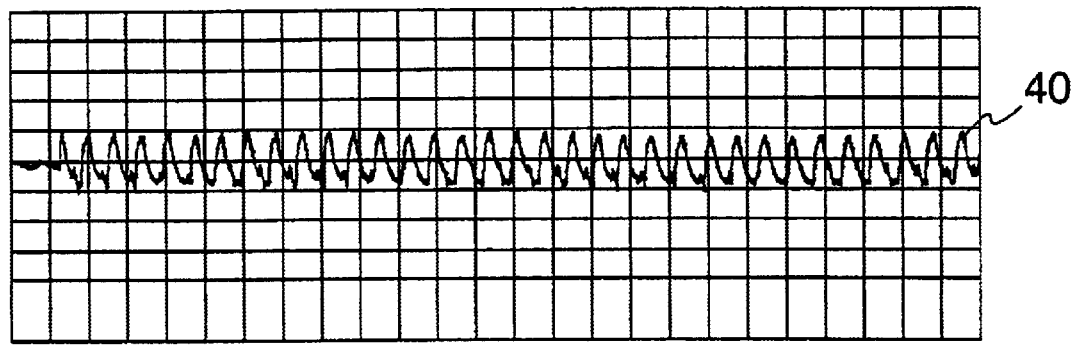
FIG. 2 illustrates the pulsatile flow created by an apparatus of the present invention.

Eight mongrel dogs were anesthetized and instrumented for CPB in accordance with standard techniques. The standard CPB circuit used a Sarns 5000 roller head and membrane oxygenators. In four animals, a valved 60 cubic centimeter bulb with a lever arm compressor was placed in the arterial return line, distal to the filter. The lever arm was set to produce a pulse rate of 60 beats per minute and a pulse pressure greater than 30 mmHg. The pressure wave 40 is illustrated FIG. 2. All animals underwent two hours of normothermic CPB without cardiac arrest, and followed for 2 hours after weaning from CPB. Activation of the pulse generator produced a pulse pressure of 41±4 mmHg, vs. 3±1 mmHg without it ($p<0.05$), although mean arterial pressures (MAP were not different between groups. Slopes (BPM/mmHg) of a best fit analysis of heart rate responses to acutely induced transients in blood pressure (30 1 130 mmHg, nitroprusside and phenylephrine) are summarized in Table 1 below.

TABLE 1

|  | Baseline | CPB | | Weaning | |
| --- | --- | --- | --- | --- | --- |
|  |  | 1 hr | 2 hr | 1 hr | 2 hr |
| Pulsatile CPB | −0.80 | −1.20 | −0.74 | −1.25 | −0.61 |
| Non-pulsatile CPB | −0.80 | −1.25 | −1.04 | −0.05 | +0.16 |

The pulsatile CPB system did not show a resetting of the baroreceptors, while the nonpulsatile system was associated with a rightward resetting of the system, and absence of sensitivity in the reflex after weaning. These data indicate that a pulse generator of the invention can be incorporated successfully in standard CPB circuits. The improved reflex control of cardiovascular function after weaning from pulsatile CPB may be important in reducing complication in some high-risk CPB patients.

EXAMPLE 2

Effect of Pulsatile vs. Non-Pulsatile CPB on Cerebral Blood Flow and Oxygen Delivery The purpose of this study was to determine the impact of pulsatile vs. non-pulsatile CPB on cerebral blood flow (CBF) and $O_2$ delivery. Nine mongrel dogs were anesthetized and instrumented for CPB. A standard CPB circuit modified as described above was used. The pulse wave generator produced a pulse rate of 60–65 beats/minute and a pulse pressure of 45±5 mmHg. All animals underwent two hours of normothermic CPB without cardiac arrest and mean arterial pressure was between 60–75 mmHg. CBF was determined at four time points (Baseline, On-Pump 5 minutes, 60 minutes, and 120 minutes) during each experiment using 10 μm radioactive microspheres. As shown in Table 2, pulsatile CPB showed a significant improvement in CBF and $O_2$ delivery as compared to non-pulsatile CPB at 60 and 120 minutes.

TABLE 2

Percent Change as compared with baseline blood flow and $O_2$ delivery.

|  | Blood Flow | $O_2$ Delivery |
| --- | --- | --- |
| 5 min pulsatile | 119.3%[1] | 74.15%[2] |
| 5 min non-pulsatile | 102.1%[1] | 20.54%[1] |
| 60 min pulsatile | 161.5%[1] | 105.41%[1] |
| 60 min non-pulsatile | −2.08%[1] | −58.32%[1] |
| 120 min pulsatile | 133.1%[1] | 90.06%[1] |
| 120 min non-pulsatile | −1.19%[1] | −38.98%[1] |

Statistical significance vs. baseline $p < 0.005$[1]; $p < 0.05$[2].

The foregoing is illustrative of the present invention, and is not to be construed as limiting thereof. The invention is defined by the following claims, with equivalents of the claims to be included therein.

That which is claimed is:

1. A cardiopulmonary bypass and extracorporeal oxygenation apparatus that provides a pulsatile blood flow output, said apparatus comprising:
   (a) a primary pump, which primary pump is a continuous pump;
   (b) an oxygenator in fluid communication with said primary pump;
   (c) a pulse wave generator in fluid communication with said oxygenator and positioned downstream from said primary pump; said pulse wave generator comprising:
      (i) a collapsible chamber having an inlet opening and an outlet opening formed therein;
      (ii) a first one-way valve connected to said inlet opening and positioned to permit the flow of blood from said primary pump through said collapsible chamber; and
   (d) a compression assembly operatively associated with said collapsible chamber and configured to alternately compress said collapsible chamber and permit the expansion of said collapsible chamber.

2. An apparatus according to claim 1, wherein said primary pump is a roller pump.

3. An apparatus according to claim 1, wherein said primary pump is a centrifugal pump.

4. An apparatus according to claim 1, further comprising a second one-way valve connected to said collapsible chamber outlet opening.

5. An apparatus according to claim 1, wherein said one-way valve is a ball valve.

6. An apparatus according to claim 1, wherein said one-way valve is a flap valve.

7. An apparatus according to claim 1, wherein said compression assembly comprises a lever arm.

8. An apparatus according to claim 1, wherein said compression assembly comprises a pneumatic compression apparatus.

9. An apparatus according to claim 1, wherein said collapsible chamber comprises a bulb.

10. An apparatus according to claim 1, wherein said collapsible chamber has a volume of about 50 to about 100 cubic centimeters.

11. A pulse-wave generator suitable for use in cardiopulmonary bypass and extracorporeal oxygenation apparatus, said pulse wave generator comprising:
   (i) a collapsible chamber having an inlet opening and an outlet opening formed therein; and
   (ii) a first one-way valve connected to said inlet opening and positioned to permit the flow of blood from, a continuous primary pump through said collapsible chamber.

12. A pulse-wave generator according to claim 11, wherein said pulse-wave generator is sterile and is sealed in an aseptic package prior to use.

13. An apparatus according to claim 11, wherein said collapsible chamber comprises a bulb.

14. An apparatus according to claim 11, wherein said collapsible chamber has a volume of about 50 to about 100 cubic centimeters.

15. A cardiopulmonary bypass and extracorporeal oxygenation apparatus that provides a pulsatile blood flow output, said apparatus comprising:
   (a) a primary pump, which primary pump is a continuous pump;
   (b) an oxygenator in fluid communication with said primary pump;
   (c) a pulse wave generator in fluid communication with said oxygenator and positioned downstream from said primary pump; said pulse wave generator comprising:
      (i) a collapsible chamber having an inlet opening and an outlet opening formed therein;
      (ii) a first one-way valve connected to said inlet opening and positioned to permit the flow of blood from said primary pump through said collapsible chamber; and
   (d) a compression assembly operatively associated with said collapsible chamber and configured to alternately compress said collapsible chamber and permit the expansion of said collapsible chamber wherein said compression assembly comprises a cam.

* * * * *